(12) United States Patent
Helfenbein et al.

(10) Patent No.: US 11,583,220 B2
(45) Date of Patent: Feb. 21, 2023

(54) TRAUMATIC BRAIN INJURY GUIDELINE SYSTEM AND METHOD

(71) Applicant: KONINKLIJKE PHILIPS N.V., Eindhoven (NL)

(72) Inventors: Eric Helfenbein, Sunnyvale, CA (US); Saeed Babaeizadeh, Arlington, MA (US)

(73) Assignee: Koninklijke Philips N.V., Eindhoven (NL)

( * ) Notice: Subject to any disclaimer, the term of this patent is extended or adjusted under 35 U.S.C. 154(b) by 118 days.

(21) Appl. No.: 15/038,052

(22) PCT Filed: Nov. 18, 2014

(86) PCT No.: PCT/IB2014/066113
§ 371 (c)(1),
(2) Date: May 20, 2016

(87) PCT Pub. No.: WO2015/075624
PCT Pub. Date: May 28, 2015

(65) Prior Publication Data
US 2016/0296155 A1 Oct. 13, 2016

Related U.S. Application Data

(60) Provisional application No. 61/906,841, filed on Nov. 20, 2013.

(51) Int. Cl.
*A61B 5/00* (2006.01)
*A61B 5/087* (2006.01)
(Continued)

(52) U.S. Cl.
CPC ............ *A61B 5/4064* (2013.01); *A61B 5/021* (2013.01); *A61B 5/082* (2013.01); *A61B 5/087* (2013.01);
(Continued)

(58) Field of Classification Search
None
See application file for complete search history.

(56) References Cited

U.S. PATENT DOCUMENTS 9,585,617 B2  3/2017  Babaeozadeh et al.
9,801,608 B2  10/2017 Weinberg et al.
(Continued)

OTHER PUBLICATIONS

Martini et al. Targeting Brain Tissue Oxygenation in Traumatic Brain Injury; Respiratory Care • Jan. 2013 vol. 58 No. 1 (Year: 2013).*

(Continued)

*Primary Examiner* — Jay B Shah

(57) ABSTRACT

A traumatic brain injury ("TBI") guideline system employing a patient monitoring sensor (30) and a patient monitoring device (10). In operation, the patient monitoring sensor (30) generates data for monitoring a TBI parameter of a patient (e.g., systolic blood pressure, blood oxygen saturation or carbon dioxide expiration of the patient), and the patient monitoring device (10) generates a TBI indicator derived from a comparison of the TBI parameter data to parameter guideline data associated with a potential TBI of the patient. The patient monitoring device (10) may include a patient data monitor module (17a) to monitor the TBI parameter data, and a TBI monitor module (17b) to generate the TBI indicator. The TBI indicator is informative of a TBI status of the patient (e.g., a hypotension status, a hypoxia status or a ventilation status of the patient), and/or a TBI treatment for the patient (e.g., a ventilation treatment for the patient).

7 Claims, 4 Drawing Sheets

(51) Int. Cl.
*A61B 5/1455* (2006.01)
*G16H 40/60* (2018.01)
*G16H 20/40* (2018.01)
*A61B 5/021* (2006.01)
*A61B 5/08* (2006.01)
*A61B 5/145* (2006.01)
*A61M 16/00* (2006.01)

(52) U.S. Cl.
CPC ...... *A61B 5/14542* (2013.01); *A61B 5/14551* (2013.01); *A61B 5/7246* (2013.01); *A61B 5/7275* (2013.01); *A61B 5/742* (2013.01); *A61M 16/0078* (2013.01); *G16H 20/40* (2018.01); *G16H 40/60* (2018.01); *A61M 2205/58* (2013.01)

(56) References Cited

U.S. PATENT DOCUMENTS

| | | |
|---|---|---|
| 2002/0087057 A1 | 7/2002 | Lovejoy et al. |
| 2003/0083582 A1 | 5/2003 | Hirsh |
| 2005/0027173 A1 | 2/2005 | Briscoe et al. |
| 2006/0155206 A1 | 7/2006 | Lynn |
| 2007/0156030 A1 | 7/2007 | Richardson |
| 2008/0281639 A1 | 11/2008 | Quinn |
| 2009/0005703 A1 | 1/2009 | Fasciano |
| 2009/0094053 A1 | 4/2009 | Jung et al. |
| 2010/0191139 A1 | 7/2010 | Jacquin et al. |
| 2010/0324429 A1 | 12/2010 | Leschinsky |
| 2012/0041330 A1 | 2/2012 | Prichep et al. |
| 2012/0197146 A1 | 8/2012 | Tan et al. |
| 2013/0150684 A1 | 6/2013 | Cooner |
| 2013/0197390 A1 | 8/2013 | Weinberg et al. |
| 2013/0261472 A1 | 10/2013 | Parkin et al. |

OTHER PUBLICATIONS

Robertson, Management of Cerebral Perfusion Pressure after Traumatic Brain Injury, Anesthesiology 2001; 95:1513-17 (Year: 2001).*

* cited by examiner

TRAUMATIC BRAIN INJURY GUIDELINE SYSTEM AND METHOD

This application is a national stage application under 35 U.S.C. § 371 of International Application No. PCT/IB2014/066113 filed on Nov. 18, 2014 and published in the English language on May 28, 2015 as International Publication No. WO/2015/075624, which claims priority to U.S. Application No. 61/906,841 filed on Nov. 20, 2013, the entire disclosures of which are incorporated herein by reference.

The present disclosure generally relates to traumatic brain injury ("TBI") guidelines, such as may be implemented/used in/with medical devices (e.g., monitors/defibrillators). The present disclosure more particularly relates to novel and inventive systems and methods for using TBI guidelines in/with a medical device (e.g., a monitor/defibrillator) to treat/care for traumatic brain injury patients.

It is estimated that approximately 1.4 million victims of traumatic brain injury are seen in emergency departments each year in the United States ("U.S.") and, of those, approximately 50,000 die and 235,000 are hospitalized. It is further estimated that at least 2% of the U.S. population has a TBI-related long-term need for help to perform activities of daily living. These statistics have inspired increased research into treatment and care of TBI patients, which has gathered growing evidence that the management of TBI in the early minutes after injury profoundly impacts outcome for the patient. This has led to the promulgation of evidence-based TBI treatment guidelines by authoritative national and international scientific bodies.

More particularly, it has been demonstrated that deleterious effects of hypoxia, hypotension, hypocapnea (caused by hyperventilation) and hypercapnea (from inadequate ventilation) often occurs soon after a traumatic brain injury. Based on these findings, the Brain Trauma Foundation has promulgated evidence-based guidelines for in-hospital and pre-hospital TBI treatment.

Generally, proper management of airway, ventilation, and hemodynamics are at the core of the TBI guidelines. The negative impact of hypoxia, hypercapnea, hypocapnea and hypovolemia are so significant that, if the earliest opportunities to intervene are missed, subsequent care, even if it is optimal, will generally not recover what was lost in neurological damage.

For example, portable monitor/defibrillators are used in a pre-hospital setting by Advanced Life Support ("ALS") or Basic Life Support ("BLS") trained medical practitioners (e.g., paramedics) to care for victims of traumatic brain injury immediately after an injury has occurred (e.g., from a fall or automobile accident, prior to arrival at the hospital). These devices can be used to monitor patient data including systolic blood pressure (SBP), blood oxygen saturation (SpO2), and expired carbon dioxide (CO2) and its derived parameter end-tidal CO2 (EtCO2).

However, many paramedics (and other medical practitioners) are not aware of the TBI guidelines, and many Emergency Medical Services ("EMS") agencies (and other medical services providers) have not formally adopted and trained their paramedics (or other medical practitioners) on the TBI guidelines. Even those paramedics (and other medical practitioners) who are trained on the TBI guidelines could still benefit from a system and method which could help them meet and maintain the TBI guidelines by providing real-time feedback and guidance. Thus, it would be beneficial to have a system and method implemented/used in/with medical devices (e.g., monitors/defibrillators) which can assist the user in maintaining monitored TBI parameters in guideline range, and can issue warnings/alerts if/when the TBI parameters fall out of guideline range.

The present disclosure recognizes that it is likely that providing TBI guideline therapy, particularly in a pre-hospital setting, will lead to dramatic improvement in outcomes for patients. From this recognition, disclosed and described herein are exemplary embodiments of the present disclosure, which, as one having ordinary skill in the art shall appreciate in view of the teachings herein, can be used together or separately to overcome the above-described needs and related challenges of the treatment and care of TBI patients.

In one exemplary embodiment of the present invention, a system is implemented in a patient monitoring device (e.g., a monitor/defibrillator) that can help the user maintain target ranges for TBI parameters based on pre-defined TBI guidelines. The system can provide warnings/alerts when the parameters fall out of a pre-defined guideline range. Such system can include software and hardware, which hardware can be used in connection with other functionality of the patient monitoring device, for example.

In one form, the system employs a patient monitoring sensor and a patient monitoring device. In operation, the patient monitoring sensor generates data for monitoring a TBI parameter of a patient (e.g., systolic blood pressure, blood oxygen saturation or carbon dioxide expiration of the patient), and the patient monitoring device generates a TBI indicator derived from a comparison of the TBI parameter data to parameter guideline data associated with monitoring a potential TBI of the patient. The patient monitoring device may include a patient data monitor to monitor the TBI parameter data, and a TBI monitor to generate the TBI indicator. The TBI indicator is informative of a TBI status of the patient (e.g., a hypotension status, a hypoxia status or a ventilation status of the patient), and/or a TBI treatment for the patient (e.g., a ventilation treatment for the patient).

The term "patient monitoring sensors" is a specific known grouping of sensors for monitoring patients including, but not limited to, blood pressure sensors, blood oxygen sensors and carbon dioxide sensors.

The term "blood pressure sensors" broadly includes sensors known prior to and subsequent to the present invention that measure blood pressure both non-invasively (e.g., through a blood pressure cuff on the arm) or invasively (e.g., with an arterial catheter pressure line.

The term "blood oxygen sensors" broadly includes sensors known prior to and subsequent to the present invention that provide an estimation of a concentration of oxygen in the blood (e.g., peripheral capillary oxygen saturation sensor) or provides a direct measurement of the concentration of oxygen in the blood (e.g., an arterial blood gas testing sensor).

The term "carbon dioxide sensor" broadly includes sensors known prior to and subsequent to the present invention that measure expired CO2 from the lungs, or direct measurements of the partial pressure of CO2 in the arterial blood PaCO2 (e.g., via an invasive blood gas sensor)

The term "patient monitoring device" is a specific known grouping of devices for monitoring patients including, but not limited, to Advanced Life Support ("ALS") monitors/defibrillators and any Automated External Defibrillators ("AED").

In another exemplary embodiment of the present invention, a method is provided that can help the user maintain target ranges for, e.g., the TBI parameters based on pre-defined TBI guidelines. The method can include providing warnings/alerts when the parameters fall out of a pre-defined guideline range. Such method can be implemented via software and hardware to run in/with a patient monitoring device (e.g., monitor/defibrillator), for example.

In one form, the method involves a patient monitoring sensor generating data for monitoring a TBI parameter of a patient, and a patient monitoring device generating a TBI indicator derived from a comparison of the TBI parameter data to parameter guideline data associated with a potential TBI of the patient. The traumatic brain injury indicator is informative of a TBI status of the patient and/or a TBI treatment for the patient.

According to the exemplary embodiments of the present invention, voice and/or display prompts can be provided to communicate information to "coach" (and/or guide, direct, suggest, etc.) the person providing care to help them meet the TBI guidelines.

The foregoing forms and other forms of the present invention as well as various features and advantages of the present disclosure will become further apparent from the following detailed description of various embodiments of the present disclosure read in conjunction with the accompanying drawings. The detailed description and drawings are merely illustrative of the present invention rather than limiting, the scope of the present disclosure being defined by the appended claims and equivalents thereof.

FIGS. 1A and 1B respectively illustrate a front view and a side view of an exemplary portable monitor/defibrillator in accordance with the present disclosure.

To facilitate an understanding of the present invention, exemplary embodiments of the present invention will be provided herein directed to an integration of a TBI monitor 17b (FIG. 2) into a controller 17 (FIG. 2) of a patient monitor device 10 (FIGS. 1 and 2) in the form of a commercially available HeartStart MRx Monitor/Defibrillator. TBI monitor 17b aids a user of patient monitor device 10 in meeting and maintaining patient care guidelines for a potential traumatic brain injury to a patient. From description of the exemplary embodiments as shown in FIGS. 1-3, those having ordinary skill in the art will appreciate how to make and use the present invention for implementation by/integration into any patient monitoring device known in the art prior to or subsequent to the present invention (e.g., any ALS monitor/defibrillator and any AED).

Figures 1A, 1B:
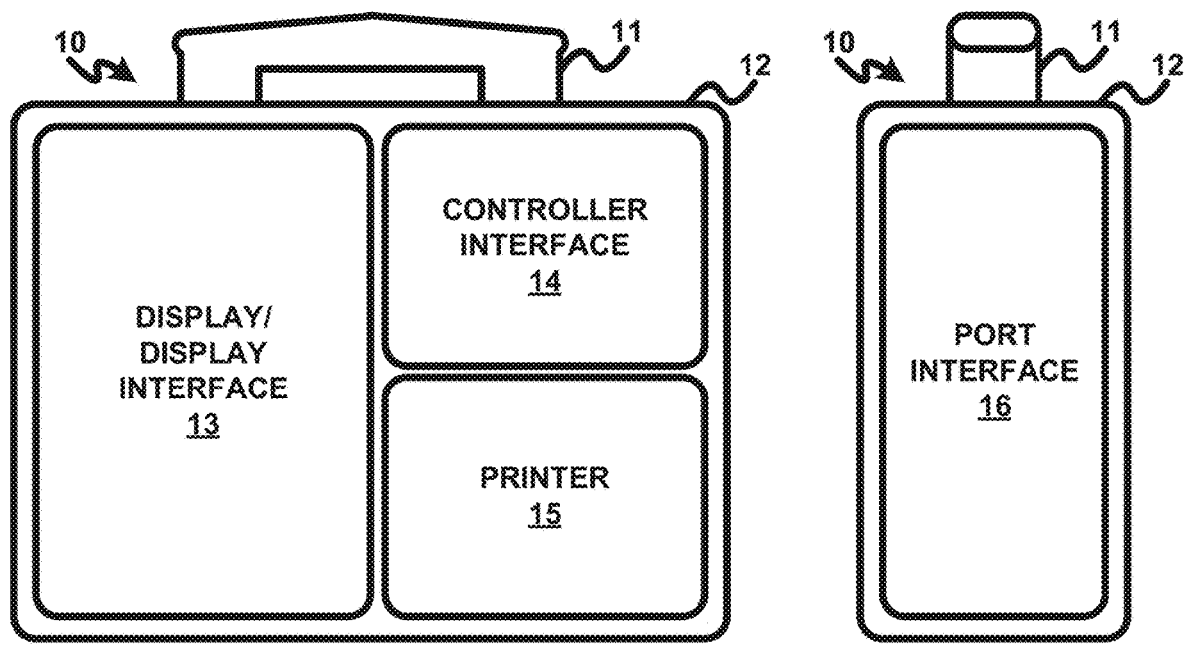
Figure 2:
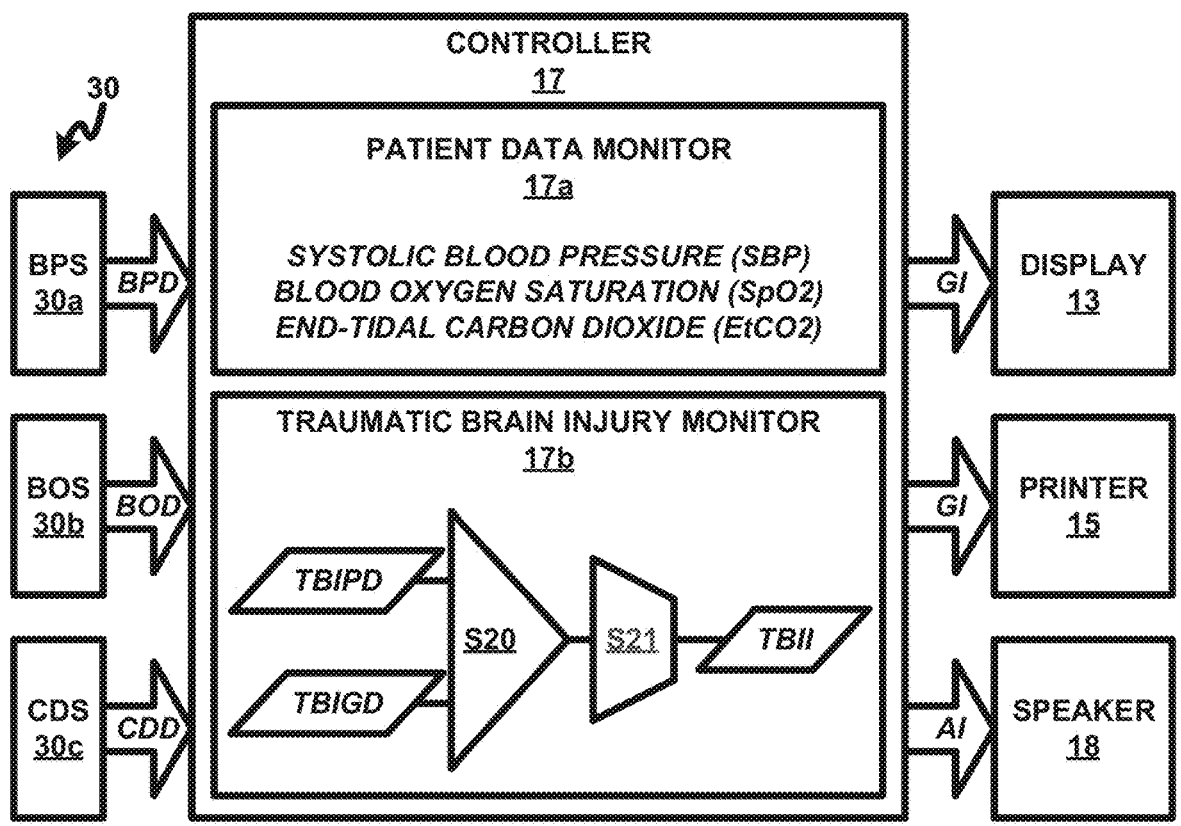
FIG. 2 illustrates a block diagram of an exemplary controller in accordance with the present disclosure.

Referring to FIGS. 1 and 2, a block diagram of patient monitoring device 10 shows a handle 11 attached to a housing 12 providing user-access to a display/display interface 13, a controller interface 14, a printer 15 and a port interface 16 as shown in FIG. 1. Housing 12 further encloses controller 17 and a speaker 18 as shown in FIG. 2.

As known in the art:
(1) display/display interface 13 displays patient monitoring data (e.g., electrocardiogram data and TBI data) as customized by a user via a display interface 13 (e.g., keys);
(2) controller interface 14 (e.g., knobs and buttons) allows the user to apply various therapies (e.g., a shock) to a patient as controlled by controller 17;
(3) printer 14 allows the user to print various patient reports, status logs and device information;
(4) port interface 16 allows for the connection by the user of one or more patient monitoring sensors 30 (FIG. 2) to controller 17 including, but not limited to, a blood pressure sensor 30a, a blood oxygen sensor 30b and a carbon dioxide sensor 30c; and
(5) controller 17 includes a patient data monitor module 17a implementing various algorithms for monitoring patient data, particularly TBI data including, but not limited to, systolic blood pressure (SBP), peripheral capillary oxygen saturation (SpO2) and end-tidal carbon dioxide (EtCO2).

This exemplary embodiment of the present invention integrates TBI monitor 17b into controller 17 for helping the user meet and maintain target ranges for TBI parameters based on pre-defined TBI guidelines. Specifically, a data flow diagram of TBI monitor 17B as shown in FIG. 2 involves a TBI parameter/guideline comparison stage S20 of a TBI parameter data TBIP to parameter guideline data TBIG associated with monitoring a potential traumatic brain injury of the patient. A TBI indicator generation stages S21 generates a TBI indicator TBII derived from the comparison of the TBI parameter data TBIP to parameter guideline data TBIG whereby TBI indicator TBII is informative of a TBI status of the patient and/or a TBI treatment for the patient. In practice, TBI indicator TBII may have any form suitable for communication to the user including, but not limited to, a graphically indicator GI for illustration by display 13 and/or for reporting by printer 15 and audio indicator AI for broadcast by speaker 17. TBI indicator TBII may also be uploaded/downloaded as required, particularly for TBI data acquisition by a laptop and for remote reporting to a hospital/care facility.

The following description is directed to non-limiting examples of a use of patient monitoring sensors 30 and patient monitoring device 10 to provide further understanding of TBI monitor 17b.

Specifically, a user initiates patient monitoring device 10 with a button press of display interface 13 and enter the patient's (approximate/estimated) age. Alternatively, the user initially can select a range for the patient's (approximate/estimated) age (e.g., "TBI age≥10") and the application continues, or "TBI age<10". If the user selects "TBI age<10", patient monitoring device 10 prompts the user to enter a more exact (approximate/estimated) age. Based on the age, patient monitoring device 10 computes the target range for TBI parameters EtCO2, SPO2, and SBP, for example. Patient data monitor 17a monitors the three (2) exemplary TBI parameters and TBI monitor 17b provides a TBI status indicator TBII for each TBI parameter indicative of whether that TBI parameter is in target range or not. Additionally, TBI monitor 17b can "coach" the user who is controlling manual ventilation rate (e.g., by manually squeezing an ambu-bag) to adjust the ventilation rate based on the current EtCO2 value to reach a target EtCO2 value. Alert warnings can be provided by TBI monitor 17b when TBI parameters are approaching or have exceeded acceptable pre-defined parameter range limits.

More particularly to the examples, when the user arrives on the scene of a patient with a potential or actual TBI:
blood pressure sensor 30a in a form of a blood pressure cuff is attached around the patient's arm and connected to port interface 16;
blood oxygen sensor 30b in a form of a SPO2 sensor is placed on the patient's finger and connected to port interface 16; and
if needed, the patient is intubated with an advanced airway or another type of airway such as an oropharyngeal airway device or mask from a bag-valve-mask (BVM) combination, or a nasal cannula (designed for CO2 monitoring as well as oxygen delivery) is placed in/on the patient, and carbon dioxide sensor 30c in a form of a CO2 sensor filter-line is applied between the airway tube and the ambu-bag (manual ventilation bag) or applied to the nasal cannula and connected to port interface 16.

The user begins TBI method by pressing a button (hardkey or softkey) of display interface 13 or controller interface 14 labeled with "TBI", for example. Patient monitoring device 10 then prompts the user to enter the patient's (estimated/approximate) age in years (and months for an infant<2 years old).

TBI monitor 17b then computes the age-based systolic blood pressure (SBP) threshold, e.g., Infants/Children age<10 yrs: [70+(age×2)] mmHg (using age in years or fractions);
Age>10 yrs: 90 mmHg.

EXAMPLES

Newborn Infant: 70 mmHg;
Infant 6 months: 71 mmHg:
5 yr. old: 80 mmHg;
>10 yrs: 90 mmHg
TBI monitor 17b uses an SPO2 threshold of 90% for all ages.
TBI monitor 17b uses an EtCO2 target range of 35-45 mmHg for all ages.

These threshold and targets are current TBI guidelines. Nonetheless, in practice, TBI monitor 17b may be configured with different values in the monitor/defibrillator configuration. It is possible that this configuration can be configurable by a user, and/or manufacturer, supplier, etc.

According to exemplary embodiments of the present invention, TBI monitor 17b may provide the TBI indicator TBII in the form of the following hypotension warnings using the current value of SBP as follows:

at threshold+10: "NOTICE: Approaching Hypotension"
at threshold+5: "WARNING: Marginal Hypotension"
at or below threshold: "ALERT!! HYPOTENSION!!"

According to exemplary embodiments of the present invention, TBI monitor 17b may provide the TBI indicator TBII in the form of the following hypoxia warnings using the current value of SPO2 as follows:

93-96%: "Insure High-Flow O2"
90-92%: "WARNING: Marginal O2 Sat"
<90%: "ALERT: !! DANGEROUS HYPOXIA!!"

One having ordinary skill in the art shall appreciate in view of teachings herein that these warnings as shown are examples. The present invention is not limited to these examples, as it has been contemplated by the inventors that the present invention can include different warnings and/or different ways that warnings are displayed and/or otherwise communicated to a user and/or recorded, stored and/or transmitted to a hospital, for example.

Further, according to exemplary embodiments of the present invention, TBI monitor 17b may guide ventilation rate by use of a metronome. For example, TBI monitor 17b may control a flashing light and/or an audio prompt to "ventilate" according to an algorithm/method that compares the current EtCO2 value to the target EtCO2 range (e.g., proportional-integral-derivative for minimizing any differential between the current EtCO2 value and the target EtCO2 range).

TBI monitor 17b start with initial ventilation rates (bpm: breaths-per-minute) according to the following patient ages, for example:

Infants (age 0-2 years): 25 bpm
Children (age 2-14 yrs.): 20 bpm
Adolescents/Adults (age 15+): 10 bpm When the current EtCO2 is above the target range (e.g., >45 mmHg), TBI monitor 17b can, e.g., display the message:

"Gently Increase Ventilation Rate"
. . . and the metronome gradually increases the rate until the target range is reached.

When the current EtCO2 is below the target range (e.g., <35 mmHg), TBI monitor 17b can, e.g., display the message:

"Gently Decrease Ventilation Rate"
. . . and the metronome gradually decreases the rate until the target range is reached.

As one having ordinary skill in the art shall appreciate in view of the teachings herein, there is usually an inverse relationship with ventilation rate and EtCO2, particularly when perfusion remains constant.

Further, exemplary embodiments of TBI monitor 17b may control a graphic display whether the three exemplary TBI parameters (SBP, SPO2, and EtCO2) are in target ranges, or close to or above/below thresholds. This can be an advantageous feature/functionality of patient monitoring device 10 in accordance with exemplary embodiments of the present invention.

For example, exemplary embodiments of TBI monitor 17b can use "Horizon Trends", similar to that which is used in some existing in-hospital patient monitors as known in the art.

Additionally, in accordance with exemplary embodiments of the present invention, it is possible to use another display modality disclosed and described herein, such as that of the novel and inventive exemplary "TBI Map" illustrated in FIG. 3.

Figure 3A:
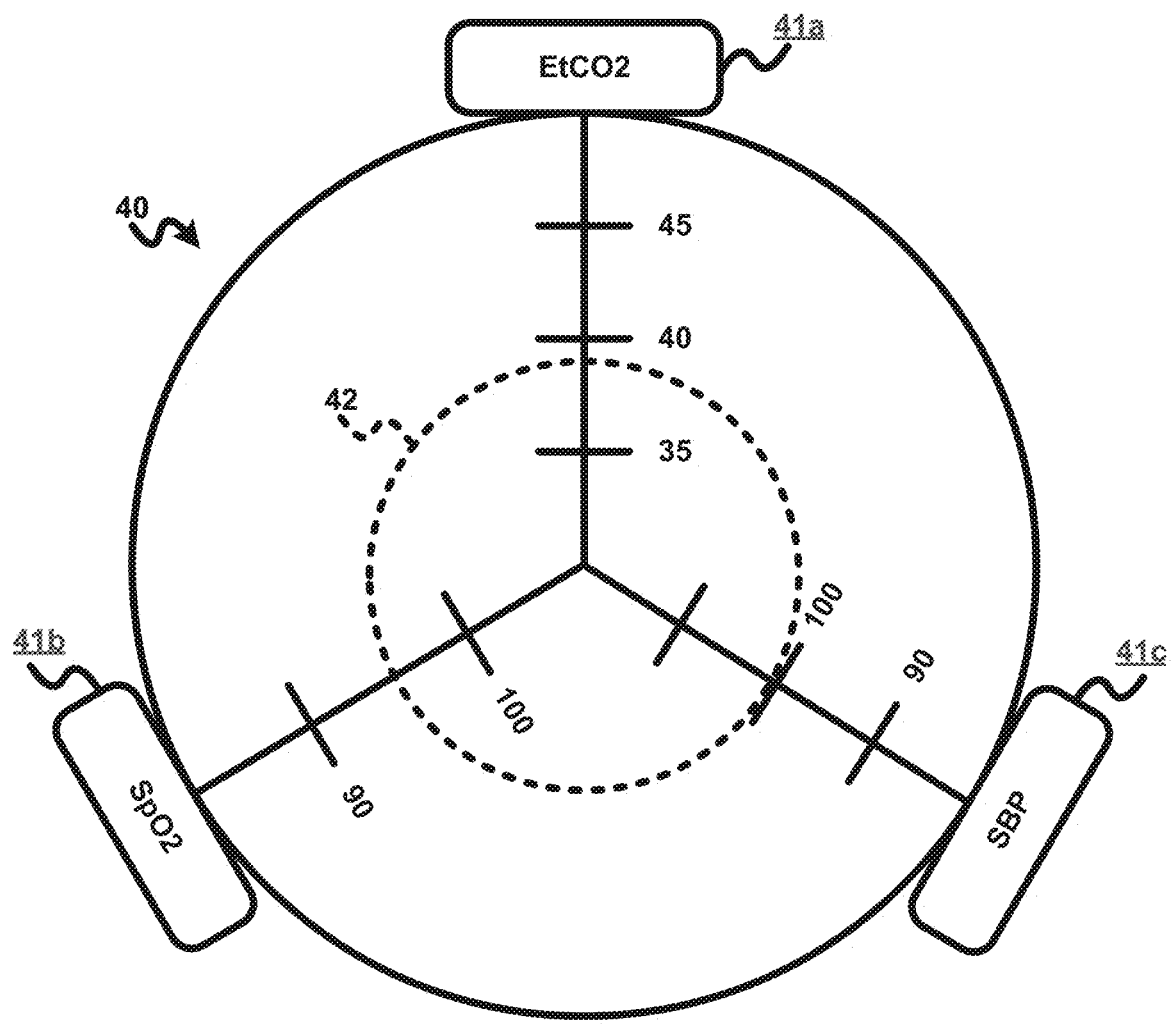
FIGS. 3A-3C illustrate an exemplary traumatic brain injury parameter map in accordance with the present disclosure for graphically representing an acceptable, warning, and dangerous TBI parameters, respectively.

Specifically, FIG. 3A illustrates a graphic representation of a TBI map 40 of a current value of the three (3) TBI parameters on a three axes labeled 41a-41c. In this example case, the three parameters are all in acceptable guideline range as illustrated by a TBI indicator 42 as a circle at the center which crosses the axes 41a-41c at the current values of the TBI parameters. In practice, TBI indicator circle 42 at the center and parameter labels 41a-41c may be colored green to represent that all parameters are in TBI guideline range.

Figure 3B:
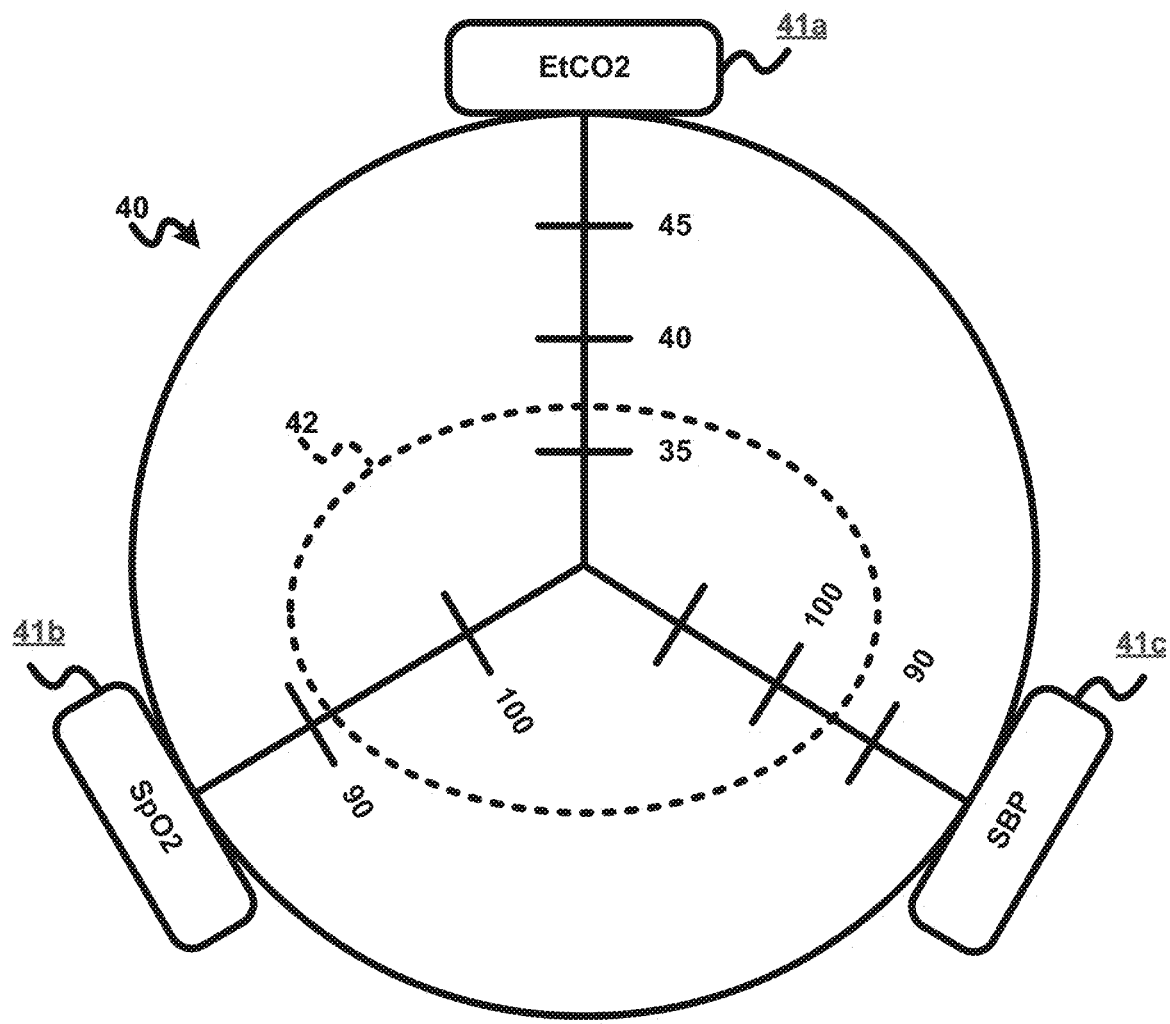

FIG. 3B illustrates a graphic representation of TBI map 40 whereby TBI parameters SpO2 and SBP are both approaching thresholds as indicated by a downward shift of TBI indicator 42 into an elliptical shape. In practice, as a warning, TBI indicator 42 and parameter labels 41b and 41c may be colored yellow to provide the warning that TBI parameters SpO2 and SBP are both approaching thresholds of the TBI guidelines, and parameter label 41a may remain green to represent TBI parameter EtCO2 is still within the guideline range.

Figure 3C:
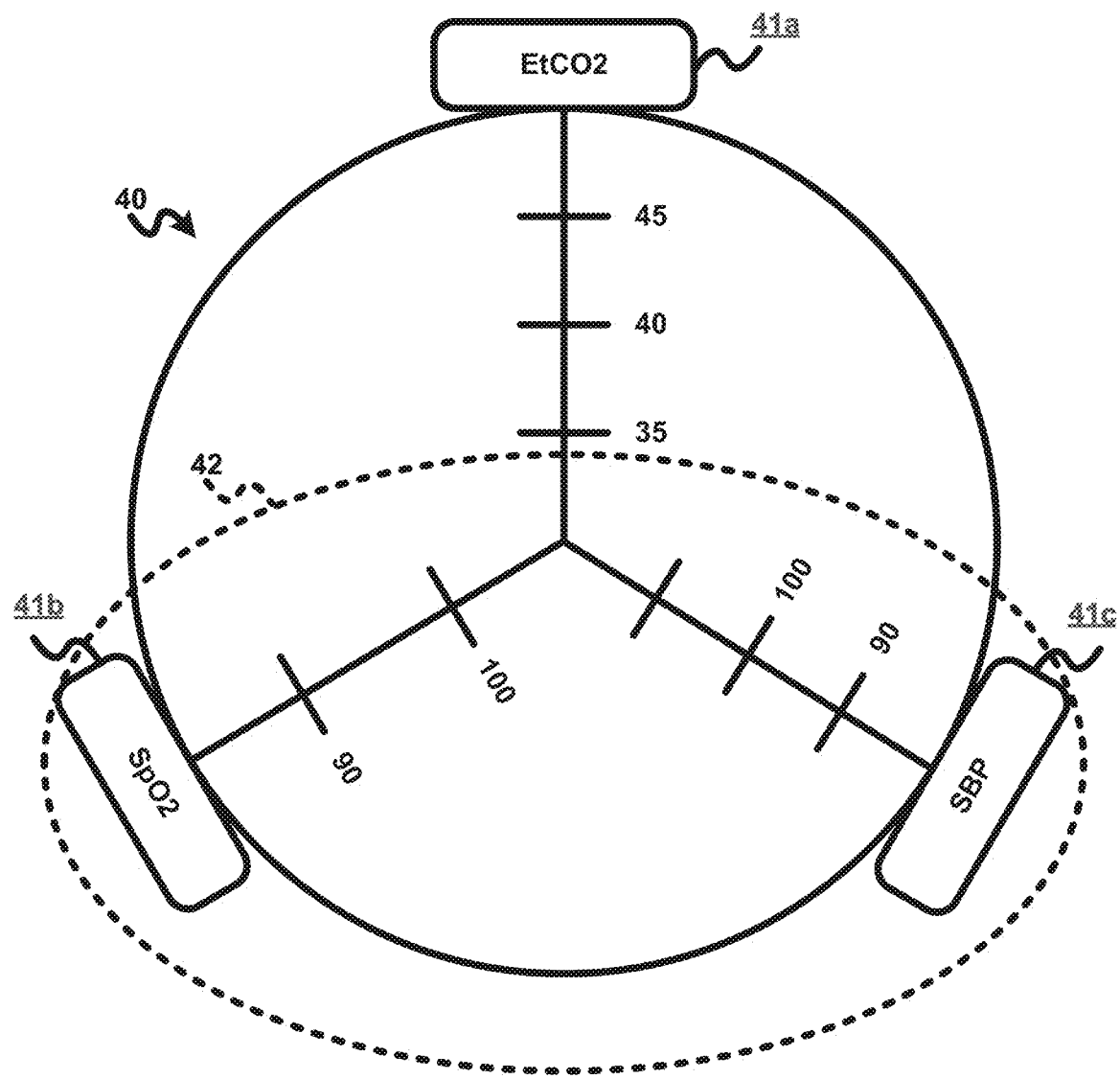

FIG. 3C illustrates a graphic representation of TBI map 40 whereby TBI parameters SpO2 and SBP are out of range as indicated by a further downward shift by TBI indicator 42 in a larger elliptical shape. In practice, as an alert, TBI indicator 42 and parameter labels 41b and 41c may be colored red to provide the alert that TBI parameters SpO2 and SBP are out of TBI guideline range, and parameter label 41a may remain green to represent TBI parameter EtCO2 is still within the guideline range.

The description and example of an exemplary indicator as shown in FIGS. 1-3, for example, is in accordance with an exemplary embodiment of a TBI indicator that represents current parameter values against the guideline range. One having ordinary skill in the art shall appreciate in view of the teachings provided herein that the above approach may be further refined, and that alternate embodiments of TBI indicators, including the information and manner in which the information is displayed or otherwise communicated, is within the scope of the present invention.

While the present invention has been described primarily with respect to monitors/defibrillator, such as pre-hospital monitors/defibrillators (e.g., used by paramedics/EMS personnel), one having ordinary skill in the art shall appreciate in view of the teaching provided herein that exemplary embodiments of the present invention can be implemented in other medical devices, including, but not limited to, patient monitors (e.g., ECG monitors), automatic external defibrillators (AEDs) and/or other defibrillators coupled to or receiving data from the necessary sensors. Indeed, exemplary embodiments of the present invention implemented in these other types of device are specifically contemplated and considered to be within the scope of the present invention.

Further, as one having ordinary skill in the art will appreciate in view of the teachings provided herein, features, elements, components, etc. described in the present disclosure/specification and/or depicted in the Figures may be implemented in various combinations of hardware and software, and provide functions which may be combined in a single element or multiple elements. For example, the functions of the various features, elements, components, etc. shown/illustrated/depicted in the Figures can be provided through the use of dedicated hardware as well as hardware capable of executing software in association with appropriate software. When provided by a processor, the functions can be provided by a single dedicated processor, by a single shared processor, or by a plurality of individual processors, some of which can be shared and/or multiplexed. Moreover, explicit use of the term "processor" or "controller" should not be construed to refer exclusively to hardware capable of executing software, and can implicitly include, without limitation, digital signal processor ("DSP") hardware, memory (e.g., read only memory ("ROM") for storing software, random access memory ("RAM"), non-volatile storage, etc.) and virtually any means and/or machine (including hardware, software, firmware, combinations thereof, etc.) which is capable of (and/or configurable) to perform and/or control a process.

Moreover, all statements herein reciting principles, aspects, and embodiments of the invention, as well as specific examples thereof, are intended to encompass both structural and functional equivalents thereof. Additionally, it is intended that such equivalents include both currently known equivalents as well as equivalents developed in the future (e.g., any elements developed that can perform the same or substantially similar function, regardless of structure). Thus, for example, it will be appreciated by one having ordinary skill in the art in view of the teachings provided herein that any block diagrams presented herein can represent conceptual views of illustrative system components and/or circuitry embodying the principles of the invention. Similarly, one having ordinary skill in the art should appreciate in view of the teachings provided herein that any flow charts, flow diagrams and the like can represent various processes which can be substantially represented in computer readable storage media and so executed by a computer, processor or other device with processing capabilities, whether or not such computer or processor is explicitly shown.

Furthermore, exemplary embodiments of the present invention can take the form of a computer program product accessible from a computer-usable and/or computer-readable storage medium providing program code and/or instructions for use by or in connection with, e.g., a computer or any instruction execution system. In accordance with the present disclosure, a computer-usable or computer readable storage medium can be any apparatus that can, e.g., include, store, communicate, propagate or transport the program for use by or in connection with the instruction execution system, apparatus or device. Such exemplary medium can be, e.g., an electronic, magnetic, optical, electromagnetic, infrared or semiconductor system (or apparatus or device) or a propagation medium. Examples of a computer-readable medium include, e.g., a semiconductor or solid state memory, magnetic tape, a removable computer diskette, a random access memory (RAM), a read-only memory (ROM), flash (drive), a rigid magnetic disk and an optical disk. Current examples of optical disks include compact disk-read only memory (CD-ROM), compact disk-read/write (CD-R/W) and DVD. Further, it should be understood that any new computer-readable medium which may hereafter be developed should also be considered as computer-readable medium as may be used or referred to in accordance with exemplary embodiments of the present invention and disclosure.

Having described preferred and exemplary embodiments of novel and inventive system and method for using traumatic brain injury guidelines in/with a monitor/defibrillator to care for traumatic brain injury patients, (which embodiments are intended to be illustrative and not limiting), it is noted that modifications and variations can be made by persons having ordinary skill in the art in light of the teachings provided herein, including the Figures. It is therefore to be understood that changes can be made in/to the preferred and exemplary embodiments of the present disclosure which are within the scope of the embodiments disclosed herein.

Moreover, it is contemplated that corresponding and/or related systems incorporating and/or implementing the device or such as may be used/implemented in a device in accordance with the present disclosure are also contemplated and considered to be within the scope of the present invention. Further, corresponding and/or related method for manufacturing and/or using a device and/or system in accordance with the present disclosure are also contemplated and considered to be within the scope of the present invention.

The invention claimed is:

1. A traumatic brain injury care method, comprising:
   managing, by a medical practitioner, at least one of an airway, a ventilation and a hemodynamics of a potential traumatic brain injury of a patient;
   generating, via a patient monitoring sensor, data indicative of the traumatic brain injury parameter of the patient;
   communicating to the medical practitioner, via a patient monitoring device, a traumatic brain injury indicator derived from a monitoring by the patient monitoring device of the traumatic brain injury parameter data relative to the traumatic brain injury parameter guideline,
      wherein the traumatic brain injury indicator is graphically informative of at least one of a traumatic brain injury status of the patient relative to the traumatic brain injury parameter guideline and a traumatic brain injury treatment for the patient relative to the traumatic brain injury parameter guideline, and wherein the medical practitioner manages the at least one of the airway, the ventilation and the hemodynamics of the potential traumatic brain injury of a patient based on the traumatic brain injury indicator.

2. The traumatic brain injury care method of claim 1, wherein generating, via the patient monitoring sensor, data indicative of the traumatic brain injury parameter of the patient includes generating, via a blood pressure sensor, generating data indicative of a systolic blood pressure of the patient; and generating, by the patient monitoring device, the traumatic brain injury indicator graphically informative of a hypotension status of the patient derived from a monitoring of the systolic blood pressure data, generated by the blood pressure sensor, relative to a blood pressure guideline associated with the monitoring of the potential traumatic brain injury of the patient.

3. The traumatic brain injury care method of claim 1, wherein generating, via the patient monitoring sensor, data indicative of the traumatic brain injury parameter of the patient includes generating, via a blood oxygen sensor, generating data indicative of a saturation of a blood oxygen of the patient; and generating, by the patient monitoring device, the traumatic brain injury indicator graphically informative of a hypoxia status of the patient derived from a monitoring of the blood oxygen saturation data, generated by the blood oxygen sensor, relative to a blood oxygen saturation guideline associated with the monitoring of the potential traumatic brain injury of the patient.

4. The traumatic brain injury care method of claim 1, wherein generating, via the patient monitoring sensor, data indicative of the traumatic brain injury parameter of the patient includes generating, via a carbon dioxide sensor, generating data indicative of an expiration level of carbon dioxide by the patient; and generating, by the patient monitoring device, the traumatic brain injury indicator graphically informative of a carbon dioxide ventilation status of the patient derived from a monitoring of an expiration of end-tidal carbon dioxide, generated by carbon dioxide sensor, relative to an end-tidal carbon dioxide guideline associated with the monitoring of the potential traumatic brain injury of the patient.

5. The traumatic brain injury care method of claim 1, wherein generating, via the patient monitoring sensor, data indicative of the traumatic brain injury parameter of the patient includes generating, via a carbon dioxide sensor, generating data indicative of an expiration level of carbon dioxide by the patient; and generating, by the patient monitoring device, the traumatic brain injury indicator graphically of a ventilation treatment for the patient derived from a monitoring of an expiration of end-tidal carbon dioxide, generated by the cardon dioxide sensor, relative to an end-tidal carbon dioxide guideline associated with the monitoring of the potential traumatic brain injury of the patient.

6. The traumatic brain injury care method of claim 1, wherein the communicating to the medical practitioner, via the patient monitoring device, the traumatic brain injury indicator includes:

displaying, by the patient monitoring device, the traumatic brain injury indicator relative to a map of the traumatic brain injury parameter guideline associated with the monitoring the potential traumatic brain injury of the patient.

7. The traumatic brain injury care method of claim 1, wherein the communicating to the medical practitioner, via the patient monitoring device, the traumatic brain injury indicator includes:

displaying, by the patient monitoring device, traumatic brain injury indicator relative to a map of the traumatic brain injury parameter guideline associated with the monitoring the potential traumatic brain injury of the patient and of at least one additional traumatic brain injury parameter guideline associated with the monitoring the potential traumatic brain injury of the patient.

\* \* \* \* \*